United States Patent [19]

Evans et al.

[11] Patent Number: 4,808,619
[45] Date of Patent: Feb. 28, 1989

[54] DI/TETRA-HYDROQUINOLINES

[75] Inventors: John M. Evans; Geoffrey Stemp, both of Harlow, England; Charles D. Nicholson; Dieter Angersbach, both of Gronau, Fed. Rep. of Germany

[73] Assignee: Beecham Group p.l.c., England

[21] Appl. No.: 892,139

[22] Filed: Jul. 30, 1986

Related U.S. Application Data

[63] Continuation-in-part of Ser. No. 717,177, Mar. 25, 1985, abandoned.

[30] Foreign Application Priority Data

Jul. 27, 1983 [GB] United Kingdom ........... 8320184
Dec. 23, 1983 [GB] United Kingdom ........... 8334415
Jul. 18, 1984 [WO] PCT Int'l Appl. ....... PCT/GB/00252
Jul. 31, 1985 [GB] United Kingdom ........... 8519306
Nov. 13, 1985 [GB] United Kingdom ........... 8527994

[51] Int. Cl.[4] ............... A61K 31/47; C07D 215/18; C07D 215/42
[52] U.S. Cl. .................. 514/278; 514/312; 514/313; 514/314; 546/18; 546/153; 546/159
[58] Field of Search ......... 514/278, 312, 313, 314; 546/18, 153, 159

[56] References Cited

U.S. PATENT DOCUMENTS 4,416,113  5/1984  Evans et al. ............ 546/16
4,427,680  1/1984  Friebe ................... 514/314
4,510,152  4/1985  Faruk ................... 514/321
4,657,910  4/1987  Morgan .................. 514/216

OTHER PUBLICATIONS

Bentue-Ferrer et al., Experimental Aging Research, 11, 137-141 (1985).

Primary Examiner—Robert J. Warden
Assistant Examiner—Robert Benson
Attorney, Agent, or Firm—Jacobs & Jacobs

[57] ABSTRACT

Compounds of the formula

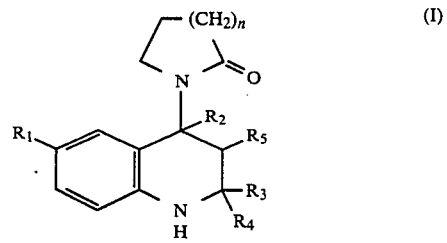

as defined in the specification, and processes for their preparation and methods of using the compounds for the treatment of hypertension in mammals, such as humans and for the treatment and/or prophylaxis of cerebrovascular disorders and/or disorders associated with cerebral senility in mammals, such as humans.

18 Claims, No Drawings

DI/TETRA-HYDROQUINOLINES

The present invention is a continuation-in-part of U.S. patent application Ser. No. 717,177, filed Mar. 25, 1985 now abandoned, which is incorporated herein by reference thereto.

The present invention relates to novel compounds having pharmacological activity, to a process for preparing them, to pharmaceutical compositions containing them, and to their use in the treatment of mammals, including man. In particular, the present invention relates to a method for the treatment of hypertension and the treatment and/or prophylaxis of cerebrovascular disorders and/or disorders associated with cerebral senility.

Accordingly, the present invention provides a compound of formula (I):

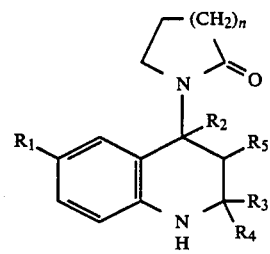

wherein:
n is 1 or 2;
$R_1$ is chloro, bromo, $C_{1-6}$alkylcarbonyl or cyano;
one of $R_3$ and $R_4$ is hydrogen or $C_{1-4}$ alkyl and the other is $C_{1-4}$ alkyl or $R_3$ and $R_4$ together are $C_{2-5}$ polymethylene;
and either
$R_5$ is hydroxy, $C_{1-3}$ alkoxy or $C_{1-8}$ acyloxy; and
$R_2$ is hydrogen and the cyclic amide moiety and $R_5$ are trans; or $R_5$ and $R_2$ together form a bond.

In preferred compounds of formula (I), n is often 1. Suitable values for $R_1$ include chloro, bromo, acetyl, propionyl, n-, and iso-butyryl and cyano. Often $R_1$ is chloro, bromo, acetyl or cyano.

The alkyl groups or alkyl moieties of alkyl-containing groups for $R_1$ are, preferably, methyl or ethyl.

Favourably, $R_3$ and $R_4$ are both alkyl having from 1 to 4 carbon atoms including methyl, ethyl or n-propyl. In particular, they are both methyl or ethyl, preferably both methyl.

Suitable examples for $R_5$ when $C_{1-3}$ alkyloxy include methoxy, ethoxy, n- and iso-propoxy, preferably methoxy.

Suitable examples for $R_5$ when acyloxy include carboxylic acyloxy such as acetoxy, propionyloxy and benzoyloxy.

There is a group of compounds within formula (I) of formula (II):

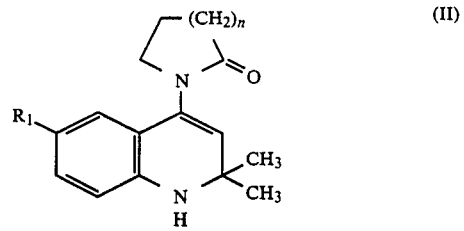

wherein variables are as defind in formula (I).

Suitable and preferred values for the variables are as described for the corresponding variables under formula (I).

It will be appreciated that there is another sub-group of compounds within formula (I) of formula (III):

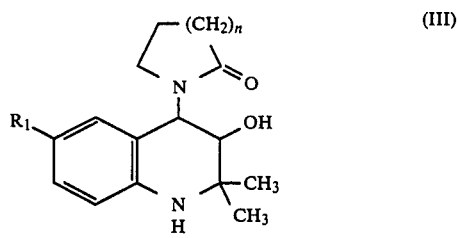

wherein the variables are as defined in formula (I).

A preferred compound of formula (I) is trans-2,2-dimethyl-6-cyano-4-(2-oxo-1-pyrrolidinyl)-1,2,3,4-tetrahydroquinolin-3-ol (Compound A).

Two other compounds of formula (I) are 6-bromo-2,2-dimethyl-4-(2-oxo-1-pyrrolidinyl)-1,2-dihydroquinoline (Compound B) and 6-cyano-2,2-dimethyl-4-(2-oxo-1-pyrrolidinyl)-1,2-dihydroquinoline (Compound C), which may be prepared as described hereinafter. Compounds B and C are novel and, as such, form part of the invention both as compounds per se and in the form of a pharmaceutical composition comprising the Compound B or C and a pharmaceutically acceptable carrier.

Other suitable compounds include:
trans-2,2-dimethyl-6-chloro-4-(2-oxo-1-pyrrolidinyl)-1,2,3,4-tetrahydroquinolin-3-ol;
6-chloro-2,2-dimethyl-4-(2-oxo-1-pyrrolidinyl)-1,2-dihydroquinoline;
trans-2,2-dimethyl-6-bromo-4-(2-oxo-1-pyrrolidinyl)-1,2,3,4-tetrahydroquinolin-3-ol.

The compounds of the invention are preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90% and still more preferably 95%.

The present invention also provides a process for the preparation of a compound of formula (I) which process comprises reacting a compound of formula (IV):

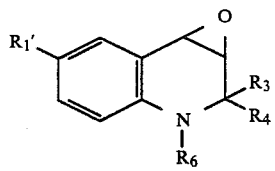 (IV)

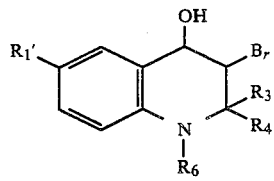 (VI)

with an anion of formula (V):

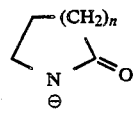 (V)

wherein
R$_1$' is R$_1$ or a group or atom convertible thereto;
R$_6$ is hydrogen or an N-protecting group;
and the remaining variables are as defined in formula (I), and thereafter if necessary converting R$_1$' to R$_1$ and/or R$_6$ to hydrogen; optionally C$_{1-3}$ alkylating or C$_{1-8}$acylating an R$_5$ hydroxy group, or dehydrating a compound of formula (I) wherein R$_5$ is hydroxy to form the compound of formula (I) wherein R$_5$ and R$_2$ together form a bond.

The reaction is suitably carried out in an inert solvent such as dimethylsulphoxide in the presence of a base, such as sodium hydride.

Conversions of R$_1$' to R$_1$ are generally known in the art of aromatic chemistry. For example, R$_1$', when halo, preferably bromo, may be converted to an R$_1$ cyano group by heating with copper (I) cyanide in an inert solvent, such as N-methylpyrrolidone. This process is preferred when R$_1$ is cyano in formula (I)

Suitable N-protecting groups R$_6$ include acyl groups such as C$_{2-5}$ alkanoyl for example acetyl and propionyl; benzoyl, phthaloyl or readily hydrogenolysable groups such as benzyl or benzyloxycarbonyl.

Preferably an R$_6$ protecting group is C$_{2-5}$ alkanoyl such as acetyl or propionyl. Such groups may be removed by conventional hydrolysis.

An R$_6$ acetyl group is particularly easily removed and may therefore under certain conditions be converted to an R$_6$ hydrogen by chromatographic methods, such as on a silica gel column.

Alkylation of R$_5$ hydroxy may be carried out using R$_5{}^1$ L$_2$ wherein L$_2$ is a leaving group. L$_2$ is a group readily displaceable by a nucleophile, preferably halo such as iodo. The reaction is carried out in an inert solvent, such as toluene, in the presence of a base, such as potassium t-butoxide.

Acylation of an R$_5$ hydroxy group may be carried out using a carboxylic acid or a derivative thereof. such as an anhydride, the reaction being carried out in a non-hydrolytic solvent in the presence of a condensation promoting agent, such as dicyclohexyl-carbodiimide.

It will be appreciated that the above acylations/alkylations at R$_5$ amy affect the substitution at the hydroquinoline nitrogen atom and appropriate modifications of reaction conditions and/or appropriate protection of should be carried out during the reaction. It will also be appreciated that such conversions may take place in any desired or necessary order.

Compounds of formula (IV) may be prepared by reacting a compound of formula (VI):

wherein the variables are as hereinbefore defined; with a base, such as potassium hydroxide, in ether or aqueous dioxan.

Compounds of the formula (VI) may be prepared in accordance with known processes, for example as described in the following Scheme:

Scheme

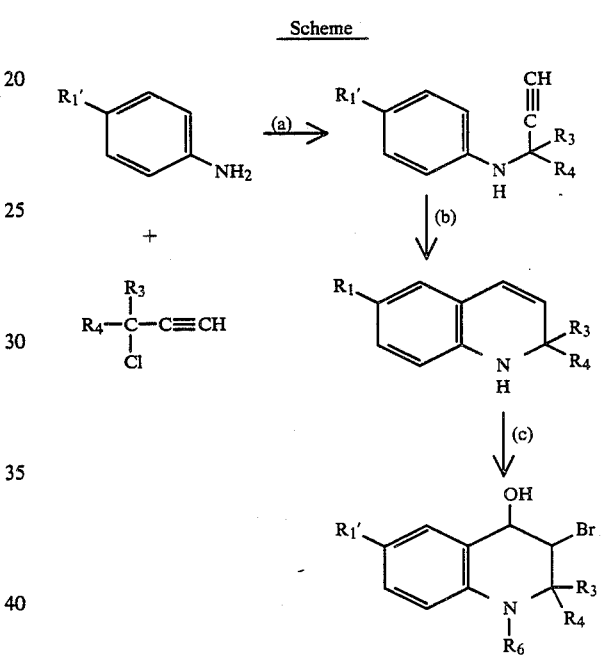

(a) Room temperature; triethylamine; copper (I) chloride, copper bronze; water; ether.
(b) Heat to 80° C.; copper (I) chloride in dioxan under N$_2$.
(c) Optional N—protection eg. acetylation with acetyl chloride in N,N—dimethylaniline in dichloromethane; then N—bromo succinimide/dimethylsulphoxide/water.

The above process can produce mixtures of compounds during reaction (b) owing to the two sites available for ring formation. It is therefore advisable to remove any of the undesired compound by, for example, chromatography, before reaction (c).

The present invention also provides a process for the preparation of compounds B and C of formula (IIa):

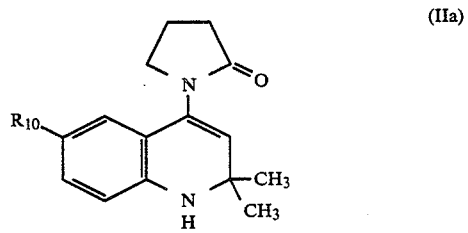 (IIa)

in which R$_{10}$ is bromo or cyano, which process comprises dehydrating a compound of formula (IVa):

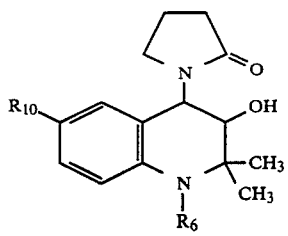

(IVa)

in which $R_6$ is hydrogen or an N-protecting group, and thereafter, if necessary, converting $R_{10}$ to other $R_{10}$ and converting $R_6$ to hydrogen.

The dehydration reaction is preferably carried out in an inert solvent such as dimethylsulphoxide in the presence of a base, such as sodium hydride.

Interconversions of $R_{10}$ are also conventional in the art. For example, $R_{10}$, when bromo, may be converted to a $R_{10}$ cyano group by heating with copper (I) cyanide in an inert solvent, such as N-methylpyrrolidone. This process is preferred when $R_1$ is cyano in formula (I).

Suitable N-protecting groups $R_6$ include acyl groups such as $C_{2-5}$ alkanoyl for example acetyl and propionyl; benzoyl, phthaloyl or readily hydrogenolysable groups such as benzyl or benzyloxycarbonyl.

Preferably an $R_6$ protecting group is $C_{2-5}$ alkanoyl such as acetyl or propionyl. Such groups may be removed by conventional hydrolysis.

An $R_6$ acetyl group is particularly easily removed and may therefore under certain conditions be converted to an $R_6$ hydrogen by chromatographic methods, such as on a silica gel column.

It will be appreciated that such conversions may take place in any desired or necessary order.

Compounds of formula (IVa) may be prepared by reacting a compound of formula (IVb):

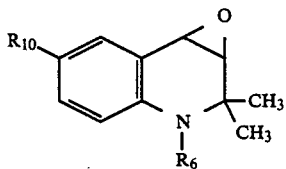

(IVb)

wherein $R_6$ and $R_{10}'$ are as defined above, with the anion:

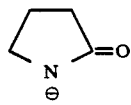

The reaction is suitably carried out in an inert solvent such as dimethylsulphoxide in the presence of a base, such as sodium hydride.

It will be appreciated that the compound of formula (IVa) may be isolated before the dehydration step, or alternatively the dehydration may be performed in situ. Under certain circumstances the dehydration will occur spontaneously.

Compounds of formula (IVb) may be prepared by reacting a compound of formula (VIa):

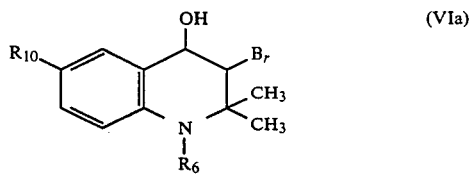

(VIa)

wherein the variables are as hereinbefore defined; with a base, such as potassium hydroxide in ether or aqueous dioxan.

Compounds of the formula (VIa) may be prepared in accordance with known processes, for example as described in the following Scheme:

Scheme

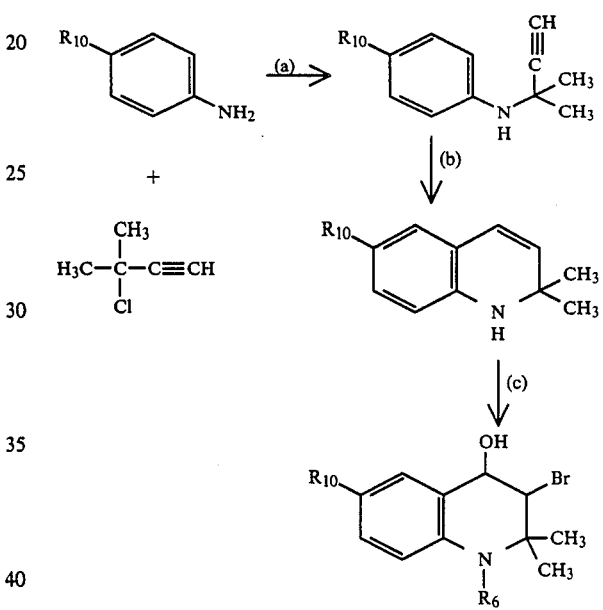

(a) Room temperature; triethylamine; copper (I) chloride, copper bronze; water; ether.
(b) Heat to 80° C.; copper (I) chloride in dioxan under $N_2$.
(c) Optional N—protection eg. acetylation with acetyl chloride in N,N—dimethylaniline in dichloromethane; then N—bromo succinimide/dimethylsulphoxide/water.

The above process can produce mixtures of compounds during reaction (b) owing to the two sites available for ring formation. It is therefore advisable to remove any of the undesired compound by, for example, chromatography, before reaction (c).

Instead of carrying out the conversion of $R_1'$ when a group or atom convertible into $R_1$ after reacting a compound of formula (IV) with an anion of formula (V), it is greatly preferred that any such conversions are carried out at an earlier stage, preferably on the dihydroquinoline produced after reaction (b) above. In other words, it is preferred that, for the process of the invention $R_1'$ is $R_1$, except when $R_1$ is cyano as hereinbefore described.

Thus, when $R_1'$ is $R_{10}$ it is preferred that $R_{10}$ is bromo, which may be converted to cyano after reacting the compound of formula (IV) with a 2-oxo-pyrrolidinyl anion, if required.

The compounds of formula (I) exist in optically active forms, and the processes of the present invention produce mixtures of such forms. The individual isomers may be separated one from another by chromatography using a chiral phase. Alternatively, an asymmetric synthesis would offer a route to the individual form.

The intermediates of formulae (IV) and (are novel and form an aspect of the present invention.

In the preparations described hereinafter, Compounds B and C are prepared via the method of Example 3 hereof. However, compounds B and C may alternatively be prepared from the novel intermediate cis-2,2-dimethyl-6-bromo-4-(2-oxo-1-pyrrolidinyl)-1,2,3,4-tetrahydroquinolin-3-ol, which is obtained as a side product in the aforesaid Example 3, and this novel intermediate also forms part of the invention.

The compounds of the formula (I) have blood-pressure lowering activity, making them of use in the treatment of hypertension. The compounds of formula (I) also have a protective effect against the consequences of cerebral metabolic inhibition and/or increase the oxygen tension of the normoxic and ischaemic cortex, making them of potential use in the treatment of a cerebrovascular disorders and disorders associated with cerebral senility in mammals including humans.

The present invention accordingly provides a pharmaceutical composition which comprises an effective amount of a compound of formula (I) and a pharmaceutically acceptable carrier. In particular, the present invention provides an anti-hypertensive pharmaceutical composition which comprises an anti-hypertensive effective amount of a compound of formula (I) and a pharmaceutically acceptable carrier.

The anti-hypertensive compositions are preferably adapted for oral administration. However, they may be adapted for other modes of administration, for example parenteral administration.

The present invention further provides a pharmaceutical composition for use in the treatment and/or prophylaxis of cerebrovascular disorders and/or disorders associated with cerebral senility, which comprises an effective amount of a compound of formula (I) and a pharmaceutically acceptable carrier.

The present invention yet further provides a method of treating hypertension in mammals including man, which comprises administering to the suffering mammal an anti-hypertensive effective amount of a compound of formula (I).

The present invention also provides a method for the treatment and/or prophylaxis of cerebrovascular disorders and/or disorders associated with cerebral senility in mammals, such as humans, which comprises administering to the mammal in need of such treatment and/or prophylaxis an effective and/or prophylactic amount of a compound of formula (I) as hereinbefore defined. The administration to the mammal may be by way of oral administration or parenteral administration.

In order to obtain consistency of administration it is preferred that an anti-hypertensive composition of the invention is in the form of a unit-dose. Suitable unit dose forms include tablets, capsules and powders in sachets or vials. Such unit dose forms may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 5 to 200 mg for a 70 kg human adult and more particularly from 10 to 100 mg.

An amount effective to treat the cerebrovascular disorders and disorders associated with cerebral senility in mammals, including humans, depends on the usual factors such as the nature and severity of the disorders being treated and the weight of the mammal. However, a unit dose will normally contain 0.1 to 100 mg for example 0.5 to 50 mg, of the compound of the invention. Unit doses will normally be administered once or more than once a day, for example 2, 3, 4, 5 or 6 times a day, more usually 1 to 4 times a day, such that the total daily dose is normally in the range, for a 70 kg adult of 0.1 to 250 mg, for example 1 to 150 mg, that is in the range of approximately 0.002 to 3.5 mg/kg/day, more usually 0.02 to 3 mg/kg/day, for example 0.7 to 2 mg/kg/day. It is greatly preferred that the compound of formula (I) is administered in the form of a unit dose composition, such as a unit dose oral or parenteral composition.

The pharmaceutical compositions of the invention are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicles and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

In addition such compositions may contain further active agents such as diuretics.

As is common practice, the compositions will usually be accompanied by written or printed directions for use in the medical treatment concerned.

DESCRIPTION 1

4-Chloro-N-(1,1-dimethyl-2-propynyl)-aniline

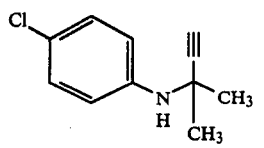

(D1)

3-Chloro-3-methyl-1-butyne (24.0 g) was added dropwise to a vigorously stirred mixture of 4-chloroaniline (25.6 g), triethylamine (20.5 g), copper (1) chloride (0.4 g), copper bronze (0.4 g), water (20 ml) and ether (100 ml), while maintaining a temperature of 15°–22° C. After stirring for 2.5 hours at room temperature, the mixture was poured into ether (200 ml) and water (100 ml). The ethereal layer was separated, and washed with water, and then brine before drying over potassium carbonate and potassium hydroxide. Removal of drying agent and solvent gave a brown oil which was distilled to give the title compound (30.0 g) which had b.pt. 68°–74′ C. at 0.06 mm Hg (G. F. Hennion and R. S. Hanzel, J.A.C.S., 82, 4908, (1960) quote b.pt. 98°–99° C. at 0.4 mm Hg);

Nmr (CDCl$_3$) 1.55 (s, 6H), 2.30 (2, 1H), 3.45 (N$\underline{H}$), 6.80 (d, J=9, 2H), 7.20 (d, J=9, 2H).

M$^{30}$ 193.660 (C$_{11}$H$_{12}$ClN requires M+ 193.0658).

DESCRIPTION 2

6-Chloro-2,2-dimethyl-1,2-dihydroquinoline

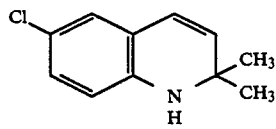

(D2)

A mixture of 4-chloro-N-(2,2-dimethyl-2-propynyl)-aniline (32.5 g) and copper (1) chloride (17.0 g) in dioxan (200 ml) was stirred at 80° C. for 2 hours, under nitrogen. The mixture was cooled, diluted with ether, and filtered. The organic phase was washed with water, then brine before drying over magnesium sulphate. Removal of drying agent and solvent, followed by distillation of the residue, gave the dihydroquinoline (18.0 g) which had b.pt 85°–100° C. at 0.06 mm Hg;

Nmr (CDCl$_3$) 1.25 (s, 6H), 3.45 (N$\underline{H}$), 5.35 (d, J=9, 1H), 6.10 (d, J=9, 1H), 6.20 (d, J=10, 1H), 6.70 (m, 2H).

M+ 193.0658 (C$_{11}$H$_{12}$NCl requires M+ 193.0658).

DESCRIPTION 3

1-Acetyl-6-chloro-2,2-dimethyl-1,2-dihydroquinoline

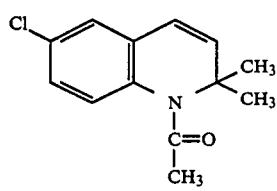

(D3)

Acetyl chloride (12 ml) was added dropwise to a stirred solution of 6-chloro-2,2-dimethyl-1,2-dihydroquinoline (16.0 g) and N,N-dimethylaniline (24 ml) in dichloromethane (200 ml) at 0° C. The solution was stirred for a further 24 hours at room temperature, then poured into water and the organic layer separated, and washed successively with IN hydrochloric acid, 5% sodium bicarbonate solution, water, brine and then dried over sodium sulphate. Removal of drying agent and solvent gave the crude N-acetyl derivative as a gum (18.9 g) having Nmr (CDCl$_3$) 1.50 (s, 6H), 2.10 (s, 3H), 5.60 (d, J=10, 1H), 6.15 (d, J=10, 1H), 6.60 (d, J=8, 1H), 6.90 (m, 2H).

M+ 235.0766 (C$_{13}$H$_{14}$ClNO requires M+ 235.0764).

DESCRIPTION 4

1-Acetyl-3-bromo-6-chloro-2,2-dimethyl-1,2,3,4-tetrahydroquinolin-4-ol

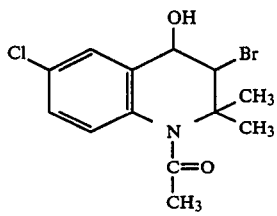

(D4)

N-Bromosuccinimide (16.0 g) was added to a vigorously stirred solution of 1-acetyl-6-chloro-2,2-dimethyl-1,2-dihydroquinoline (18.9 g) in dimethyl sulphoxide (150 ml) containing water (15 ml). The mixture was stirred for 1 hour at room temperature, then diluted with water and extracted into ethyl acetate. The organic extracts were washed with water and brine, then dried over sodium sulphate. Removal of drying agent and solvent gave the bromohydrin as a gum (26.5 ) which had Nmr (CDCl$_3$) 1.70 (s, 6H), 2.10 (s, 3H), 3.30 (O$\underline{H}$), 3.80 (d, J=9, 1H), 4.70 (d, J=9, 1H), 6.75 (d, J=8, 1H), 7.10 (dd, J=8, 2, 1H), 7.45 (d, J=2, 1H).

M+ 330.9972 (C$_{13}$H$_{15}$BrClNO$_2$ requires M+, 330.9975).

DESCRIPTION 5

1-Acetyl-6-chloro-2,2-dimethyl-3,4-epoxy-1,2,3,4-tetrahydroquinoline

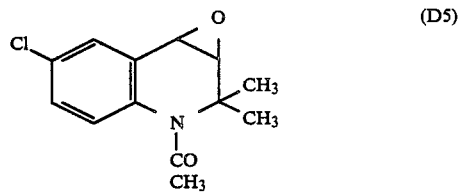

(D5)

A mixture of 1-acetyl-3-bromo-6-chloro-2,2-dimethyl-1,2,3,4-tetrahydroquinolin-4-ol (26.5 g) and potassium hydroxide pellets (25.0 g) in dry ether (500 ml) was vigorously stirred at room temperature for 48 hours. The solution was filtered and evaporated in vacuo to give the epoxide (18.5 g) as a gum having Nmr (CDCl$_3$) 1.20 (s, 3H), 1.85 (s, 3H), 2.10 (s, 3H), 3.35 (d, J=4, 1H), 3.75 (d, J=4, 1H), 6.65 (d, J=9, 1H), 7.15 (m, 2H).

EXAMPLE 1

Trans-2,2-dimethyl-6-chloro-4-(2-oxo-pyrrolidinyl)-1,2,3,4,-tetrahydroquinolin-3-ol

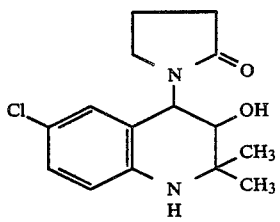

(1)

To a suspension of sodium hydride (450 mg of 80% dispersion in oil) in dry dimethylsulphoxide (20 ml) was added 2-pyrrolidinone (1.2 g) in dimethylsulphoxide (20 ml) and the mixture was then stirred at room temperature, under nitrogen, for 1 hour. A solution of 1-acetyl 6-chloro-2,2-dimethyl 3,4-epoxy-1,2,3,4-tetrahydroquinoline (2.5 g) in dimethyl sulphoxide was then added dropwise, and the solution stirred for 24 hours at room temperature. The mixture was then poured into water and extracted into ethyl acetate. The combined organic layers were washed with water, then brine, and dried over sodium sulphate. Removal of solvent and drying agent, followed by chromatography of the residue on a silica gel column eluted with mixtures of chloroform and methanol, gave the title compound as a yellow foam (1.1 g) which recrystallized from 60-80 petrol-ethyl acetate (9:1) as colourless mircoprisms (0.24 g) having m.pt. 82°-85° C.;

Nmr (CDCl$_3$) 1.20 (s, 3H), 1.30 (s, 3H), 2.10 (m, 2H), 2.55 (m, 2H), 2.80 (OH), 3.20 (m, 2H), 3.65 (d, J=10, 1H), 3.75 (NH), 5.25 (d, J=10, 1H), 6.45 (d, J=8, 1H), 6.95 (m, 2H).

M+ 294.1134 (C$_{15}$H$_{19}$N$_2$O$_2$Cl requires M+ 294.1134).

EXAMPLE 2

6-Chloro-2,2-dimethyl-4-(2-oxo-pyrrolidinyl)-1,2-dihydroquinoline

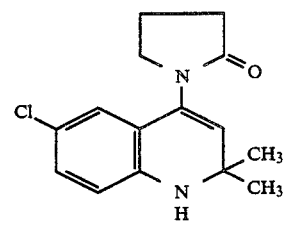

(2)

From the reaction between 2-pyrrolidinone and 6-chloro-2,2-dimethyl-3,4-epoxy-1,2,3,4-tetrahydroquinoline described in Example 1, investigation of the earlier chromatographic fractions gave the title compound as a yellow foam, which recrystallised from 60-80 petrol-ethyl acetate (9:1) as yellow plates (0.8 g) having m.pt. 158°-9° C.;

Nmr (CDCl$_3$) 1.35 (s, 6H), 2.20 (m, 2H), 2.50 (m, 2H), 3.60 (t, J=6, 2H), 3.75 (NH), 5.50 (s, 1H), 6.40 (d, J=8, 1H), 6.75 (d, J=2, 1H), 6.95 (dd, J=8, 2, 1H).

M+ 276.1008 (C$_{15}$H$_{17}$N$_2$OCl requires M+ 276.1010).

Anal. Found: C, 65.09; H, 6.18; N, 10.14; C$_{15}$H$_{17}$N$_2$OCl requires C, 65.10; H, 6.19; N, 10.12.

EXAMPLE 3

Trans-2,2-dimethyl-6-bromo-4-(2-oxo-pyrrolidinyl)-1,2,3,4-tetrahydroquinolin-3-ol

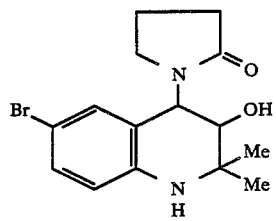

(3)

By an analogous procedure to that found in Example 1, reaction between 2-pyrrolidinone (3,4 g) and 1-acetyl-6-bromo-2,2-dimethyl-3,4-epoxy-1,2,3,4-tetrahydroquinoline (12.0 g) using sodium hydride (1.5 g) as base in dimethylsulphoxide (70 ml) gave the title compound, after chromatography, as an off-white foam (0.7 g) having m.pt. 93°-102° C.

Nmr (CDCl$_3$) 1.20 (s, 3H), 1.35 (s, 3H), 2.20 (m, 2H), 2.60 (m, 2H), 3.20 (m, 2H), 3.60 (OH, NH), 3.70 (d, J=10, 1H), 5.20 (d, J=10, 1H), 6.40 (d, J=8, 1H), 7.10 (m, 2H).

M+ 338.0639 (C$_{15}$H$_{19}$N$_2$O$_2$Br requires M+ 338.0630).

EXAMPLE 4

Trans-2,2-dimethyl-6-cyano-4-(2-oxo-pyrrolidinyl)-1,2,3,4-tetrahydroquinolin-3-ol Compound A

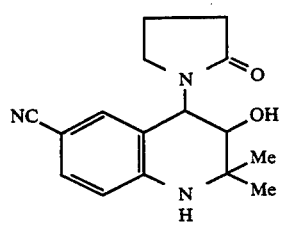

(4)

A solution of trans-2,2-dimethyl-6-bromo-4-(2-oxo-pyrrolidinyl)-1,2,3,4-tetrahydroquinolin-3-ol (0.37 g), and copper (1) cyanide (0.2 g) in N-methylpyrrolidone (10 ml) was heated under reflux for 4 h. After cooling, the mixture was poured into 10% aqueous ethylenediamine (50 ml) and extracted into ethyl acetate. The combined extracts were washed with water, and dried over magnesium sulphate. Removal of solvent and drying agent, followed by crystallisation of the residue from ethyl acetate gave the title compound as off-white microcrystals (76 mg) having m.pt. 297°–298° C.;

Nmr (DMSO-d$_6$) 1.10 (s, 3H), 1.30 (s, 3H), 2.00 (m, 2H), 2.35 (m, 2H), 3.00–3.75 (m, hidden by H$_2$O, 3H), 4.90 (d, J=10, 1H), 5.35 (d, J=4, 1H, exchangeable with D$_2$O), 6.65 (d, J=8, 1H), 6.80 (s, 1H, exchangeable with D$_2$O), 7.05 (m, 1H), 7.36 (dd, J=8, 2, 1H).

M+ 285.1481 (C$_{16}$H$_{19}$N$_3$O$_2$ requires M+ 285.1477).

Anal. Found: C, 67.35; H, 6.74; N, 14.64; C$_{16}$H$_{19}$N$_3$O$_2$ requires C, 67.35; H, 6.71; N, 14.73.

Pharmacological Data

Systolic blood pressure was recorded by a modification of the tail cuff method described by I M Claxton, M G Palfreyman, R H Poyser, R L Whiting, European Journal of Pharmacology, 37, 179 (1976). W+W BP recorder, model 8005, was used to display pulses Prior to all measurements rats were placed in a heated environment (33.5±0.5° C.) before transfer to a restraining cage. Each determination of blood pressure was the mean of at least 6 readings. Spontaneously hypertensive rats (ages 12–18 weeks) with systolic blood pressure >170 mmHg were considered hypertensive.

TABLE I

| | Time Post Dose Hours | % Change in Systolic Blood | % Change in Heart Rate |
|---|---|---|---|
| Compound of Example 4 | | | |
| 6 rats | | | |
| Dose 3 mg/kg | 1 | −2 ± 6 | −4 ± 4 |
| p.o. | 2 | −8 ± 6 | −11 ± 2 |
| Initial Blood | 4 | −26 ± 5 | −6 ± 6 |
| Pressure | 6 | −19 ± 4 | −7 ± 5 |
| 209 ± 6 mmHg | | | |
| Initial Heart | 24 | −3 ± 9 | −5 ± 6 |
| Rate | | | |
| 465 ± 16 beats/min | | | |
| Compound of Example 1 | | | |
| 6 rats | | | |
| Dose 10 mg/kg | 1 | −25 ± 1 | 3 ± 2 |
| p.o. | 2* | −18 ± 3 | 1 ± 3 |
| Initial Blood | 4 | −16 ± 4 | −6 ± 2 |
| Pressure | 6 | −10 ± 4 | −4 ± 3 |
| 246 ± 8 mmHg | | | |

TABLE I-continued

| | Time Post Dose Hours | % Change in Systolic Blood | % Change in Heart Rate |
|---|---|---|---|
| Initial Heart Rate | | | |
| 491 ± 14 beats/min | | | |

The following pharmacological data illustrate the activity of a compound of formula (I) in tests which are indicative of compounds of potential use in the treatment of cerebrovascular disorders associated with cerebral senility in mammals. The following Examples illustrate the preparation of compounds B and C.

Pharmacological Data

1. Triethyltin-induced cerebral oedema in the rat.

The cerebral oedema is induced by oral administrations repeated for 5 consecutive days—one administration per day—of triethyltin chloride at a dose of 2 mg/kg. The test compound is also administered orally twice daily as aqueous solution or suspension (1 ml/100 g body-weight); these adminstrations are given during the 5 days of intoxication with tin. Three groups of 10 male specific pathogen-free (SPF) Wistar rats of 280 ±10 g body-weight are used:

1 control group
 1 group intoxicated with triethyltin
 1 group intoxicated with triethyltin and treated with the studied compound.

The rats are killed on the evening of the fifth day; the brain is removed, weighed fresh and after desiccation to constant weight and the water content of each brain is calculated:

[H$_2$O] = fresh weight − dry weight.

The following are then calculated:
the mean water content (M±Sm%) of each group;
the protection index P due to the administered compound:

$$P\% = 1 - \frac{[H_2O]\text{treated group} - [H_2O]\text{control group}}{[H_2O]\text{triethyltin group} - [H_2O]\text{control group}} \times 100$$

The significance is evaluated by the Mann-Whitney test.

The results are shown in Table II

TABLE II

| Compound | Dosage mg/kg p.o. | % inhibition of cerebral oedema formation |
|---|---|---|
| A | 2 × 2.5 | 30* |
| B | 2 × 1 | 41.4** |
| | 2 × 12.5 | 100** |
| C | 2 × 1 | 53.3** |
| | 2 × 12.5 | 100** |

Statistical significance
*p < 0.05
**p < 0.01

2. Effect of test compound on oxygen tension (pO$_2$) of rat cortex.

(A) Animal Preparation.

Male rats (280–350 g) were anaesthetized with sodium-thio pentone (100 mg/kg i.p.). The arterial blood pressure was recorded from a femoral artery.

(B) Measurement.

The cranium was opened with a trephine (0.6 mm) above the praecentral cortex. The dura mata was carefully removed and a multiwire oxygen sensitive electrode was placed on the cortex.

The electrode current was continuously recorded.

After a stabilisation period the test compound was administered. The change in the cortical $pO_2$, produced by compound administration, was calculated for each animal.

These measurements were performed in normal animals and in animals in which both carotid arteries had been ligated 3 weeks previously in order to induce cortical ischaemia.

(C) Results.

The results for Compound A are shown in Table III

TABLE III

| Dosage mg/kg i.v. | N | Increase in $pO_2$ (torr) | Ischaemic Cortex Increase in $pO_2$ (torr) (mean ± sem) |
| --- | --- | --- | --- |
| 0.4 | 3 | 2.1 ± 2.0 | |
| 0.5 | 5 | | 0.9 ± 0.9 |
| 0.8 | 2 | 4.1 ± 0.9 | |
| 1.0 | 5 | | 1.9 ± 1.9 |

The above results show that Compound A increases $pO_2$ in the rat normoxic and chronic ischaemic cortex.

All results in Table III are statistically significant ($p < 0.05$)

EXAMPLE 5

6-Bromo-2,2-dimethyl-4-(2-oxo-1-pyrrolidinyl)-1,2-dihydroquinoline (Compound B)

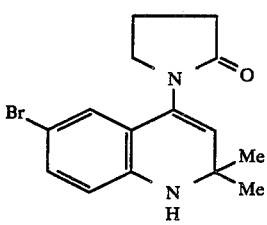

During certain runs of the preparation of trans-2,2-dimethyl-6-bromo-4-(2-oxo-1-pyrrolidinyl)-1,2,3,4-tetrahydroquinolin-3-ol (as described in Example 3) investigation of the earlier chromatographic fractions in the purification of that compound, revealed the presence of cis-6-bromo-2,2-dimethyl-4-(2-oxo-1-pyrrolidinyl)-1,2,3,4-tetrahydroquinolin-3-ol, and 6-bromo-2,2-dimethyl-4-(2-oxo-1-pyrrolidinyl)-1,2-dihydroquinoline (compound B) which was obtained as crystals from ethyl acetate-pentane: m.p. 177°–178° C.

NMR (CDCl$_3$) δ: 1.32 (s, 6H), 1.93–2.70 (series of m, 4H), 3.50 (t, J=7 Hz, 2H), 3.87 (br m, 1H), 5.37 (s, 1H), 6.23 (d, J=8 Hz, 1H), 6.73 (d, J=2 Hz, 1H), 6.93 (q, J=8, 2 Hz, 1H).

EXAMPLE 6

6-cyano-2,2-dimethyl-4-(2-oxo-1-pyrrolidinyl)-1,2-dihydroquinoline (Compound C)

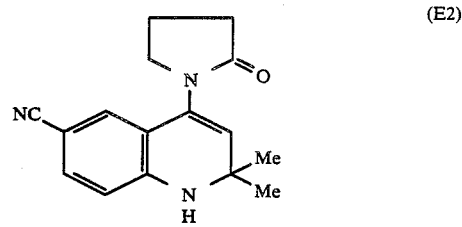

6-Bromo-2,2-dimethyl-4-(2-oxo-1-pyrrolidinyl)-1,2-dihydroquinoline (0.50 g) and copper (1) cyanide were heated under reflux in N-methylpyrrolidone (15 ml) for 4 hours. The mixture was poured into 30% aqueous ethylenediamine (25 ml) and extracted with ethyl acetate. The organic phase was washed with aqueous ethylenediamine, water and brine and dried over anhydrous magnesium sulphate. Filtration and evaporation gave a gum (0.40) which was combined with the crude product (0.23) of another run and chromatographed (chromatotron; 30% ethyl acetate-pentane ethyl acetate in a gradient elution). Fractions containing the desired material were combined and recrystallised from ethyl acetate-pentane as a yellow solid (0.19 g) of m.p. 207°–209° C.

NMR (CDCl$_3$) δ: 1.39 (s, 6H), 2.11–2.66 (m, 4H), 3.60 (t, 7 Hz, 2H), 4.00 (br m, 1H), 5.50 (s, 1H), 6.50 (d, J=9, 1H), 7.01 (d, J=2, 1H), 7.21 (q, J=9, 2 Hz, 1H).

We claim:

1. A compound of formula (I):

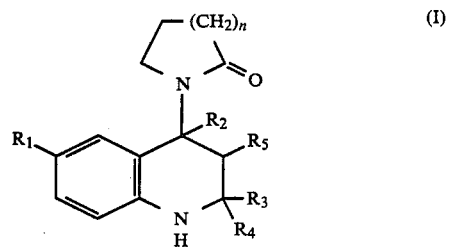

wherein:

n is 1 or 2;

$R_1$ is chloro, bromo, $C_{1-6}$ alkylcarbonyl or cyano;

one of $R_3$ and $R_4$ is hydrogen or $C_{1-4}$ alkyl and the other is $C_{1-4}$ alkyl or $R_3$ and $R_4$ together are $C_{2-5}$ polymethylene;

and either;

$R_5$ is hydroxy, $C_{1-3}$ alkoxy or $C_{1-8}$ acyloxy; and $R_2$ is hydrogen and the cyclic amide moiety and $R_5$ are trans; or $R_5$ and $R_2$ together form a bond.

2. A compound according to claim 1, wherein $R_3$ and $R_4$ are both methyl.

3. A compound according to claim 1 of formula (III):

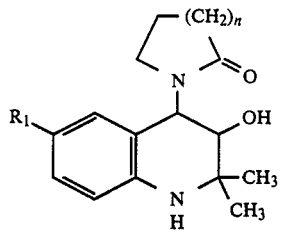

wherein R₁ and n are as defined in formula (I).

4. A compound according to claim 1, wherein n is 1.

5. A compound according to claim 1, wherein R₁ is chloro, bromo, acetyl or cyano.

6. 6-Bromo-2,2-dimethyl-4-(2-oxo-1-pyrrolidinyl)-1,2-dihydroquinoline,
6-cyano-2,2-dimethyl-4-(2-oxo-1-pyrrolidinyl)-1,2-dihydroquinoline,
trans-2,2-dimethyl-6-cyano-4-(2-oxo-1-pyrrolidinyl)-1,2,3,4-tetrahydroquinolin-3-ol,
trans-2,2-dimethyl-6-chloro-4-(2-oxo-1-pyrrolidinyl)-1,2,3,4-tetrahydroquinolin-3-ol,
6-chloro-2,2-dimethyl-4-(2-oxo-1-pyrrolidinyl)-1,2-dihydroquinoline or
trans-2,2-dimethyl-6-bromo-4-(2-oxo-1-pyrrolidinyl)-1,2,3,4-tetrahydroquinolin-3-ol.

7. Trans-2,2-Dimethyl-6-bromo-4-(2-oxo-1-pyrrolidinyl)-1,2,3,4-tetrahydroquinolin-3-ol.

8. An anti-hypertensive pharmaceutical composition comprising an anti-hypertensive effective amount of a compound according to claim 1 and a pharmaceutically acceptable carrier.

9. A method of treating hypertension in mammals including man, which comprises administering to the suffering mammal an anti-hypertensive effective amount of a compound according to claim 1.

10. A pharmaceutical composition for the treatment and/or prophylaxis of cerebrovascular disorders and-/or disorders associated with cerebral senility in mammals, such as humans, comprising an effective and/or prophylactic amount of a compound according to claim 1 and a pharmaceutically acceptable carrier.

11. A method for the treatment and/or prophylaxis of cerebrovascular disorders and/or disorders associated with cerebral senility in mammals, such as humans, which comprises administering to the mammal in need of such treatment and/or prophylaxis an effective and-/or prophylactic amount of a compound according to claim 1.

12. A method according to claim 11, wherein n is 1.

13. A method according to claim 11, wherein R₁ is chloro, bromo or cyano.

14. A method according to claim 11, wherein R₃ and R₄ are both methyl.

15. A method according to claim 11, wherein R₂ and R₅ together form a bond.

16. A method according to claim 11, wherein R₂ is hydrogen and R₅ is hydroxy.

17. A method according to claim 11, wherein the compound of formula (I) is 6-bromo-2,2-dimethyl-4-(2-oxo-1-pyrrolidinyl)-1,2-dihydroquinoline,
6-cyano-2,2-dimethyl-4-(2-oxo-1-pyrrolidinyl)-1,2-dihydroquinoline,
trans-2,2-dimethyl-6-cyano-4-(2-oxo-1-pyrrolidinyl)-1,2,3,4-tetrahydroquinolin-3-ol,
trans-2,2-dimethyl-6-chloro-4-(2-oxo-1-pyrrolidinyl)-1,2,3,4-tetrahudroquinolin-3-ol,
6-chloro-2,2-dimethyl-4-(2-oxo-1-pyrrolidinyl)-1,2-dihydroquinoline or
trans-2,2-dimethyl-6-bromo-4-(2-oxo-1-pyrrolidinyl)-1,2,3,4-tetrahydroquinolin-3-ol.

18. A method according to claim 11, wherein the compound of formula (I) is 6-bromo-2,2-dimethyl-4-(2-oxo-1-pyrrolidinyl)-1,2-dihydroquinoline or 6-cyano-2,2-dimethyl-4-(2-oxo-1-pyrrolidinyl)-1,2-dihydroquinoline.

* * * * *